(12) United States Patent
Rönspeck et al.

(10) Patent No.: US 6,994,970 B1
(45) Date of Patent: Feb. 7, 2006

(54) PEPTIDES FOR COMBATING THE AUTOANTIBODIES THAT ARE RESPONSIBLE FOR DILATATIVE CARDIOMYOPATHY (DCM)

(75) Inventors: Wolfgang Rönspeck, Berlin (DE); Rudolf Kunze, Stegelitz (DE); Gerd Wallukat, Berlin (DE); Manuela Dierenfeld, Blankenfelde (DE)

(73) Assignee: Fresenius Medical Care Affina GmbH, Berlin (DE)

( * ) Notice: Subject to any disclaimer, the term of this patent is extended or adjusted under 35 U.S.C. 154(b) by 380 days.

(21) Appl. No.: 10/088,681

(22) PCT Filed: Sep. 21, 2000

(86) PCT No.: PCT/EP00/09241

§ 371 (c)(1),
(2), (4) Date: Jun. 21, 2002

(87) PCT Pub. No.: WO01/21660

PCT Pub. Date: Mar. 29, 2001

(30) Foreign Application Priority Data

Sep. 21, 1999 (EP) ................................. 99118630
Sep. 21, 1999 (EP) ................................. 99118631

(51) Int. Cl.
*A61K 38/00* (2006.01)
(52) U.S. Cl. ........................................... 435/6
(58) Field of Classification Search ..................... 435/6
See application file for complete search history.

(56) References Cited

PUBLICATIONS

Rudikoff et al. Single amino acid substitution altering antigen-binding specificity. Proc Natl Acad U S A. Mar. 1982; 79(6):1979-83.*
Schneider et al. "Peptide design by artifical neural networks and computer-based evolutionary search ", XP-002127398, *Proc. Natl. Acad. Sci. USA, Biochemistry*, vol. 95 (Oct. 1998), pp. 12179-12184.
Liu et al., "Screening of Serum Autoantibodies to Cardiac $\beta_1$-adrenoceptors and $M_2$-muscarinic Acetylcholine Receptors in 408 Healthy Subjects Varying Ages"., XP-000929153, *Toimmunity*(1999) 29 (1) pp. 43-51.
Elies et al., "Structural and Functional Analysis of the B Cell Epitopes Recognized by Anti-Receptor Autoantibodies in Patients with Chagas Disease',"  XP-002142657, *Journal of Immunology* (Nov. 1, 1996) 157 (9), pp. 4203-4211.
Wallukat et al., "Agonistic Effects of Anti-Peptide Antibodies and Autoantibodies Directed Against Adrenergic and Cholinergic Receptors: Abscence of Desensitization", XP-000929115, *Blood Pressure Supplement*(1996) 3 pp. 31-36.

* cited by examiner

*Primary Examiner*—Christopher R. Tate
*Assistant Examiner*—Maury Audet
(74) *Attorney, Agent, or Firm*—Jacobson Holman PLLC

(57) ABSTRACT

Peptides which bind auto-antibodies being in a causally pathological relationship with dilatative cardiomyopathy are described. The peptides may be bound, for example, to a solid phase. Auto-antibodies can be removed by treating blood of patients suffering from DCM with the peptides according to the invention.

10 Claims, No Drawings

PEPTIDES FOR COMBATING THE AUTOANTIBODIES THAT ARE RESPONSIBLE FOR DILATATIVE CARDIOMYOPATHY (DCM)

This is a 371 of PCT/EP00/09241, filed Sep. 21, 2000, the disclosure of which is incorporated herein by reference.

The present invention relates to peptides against auto-antibodies causing DCM, medicaments containing such peptides, the use of the peptides, methods for the treatment of diseases related to $\beta_1$-adrenergically active auto-antibodies, and a device for immunoadsorption containing the peptides bound to a solid phase.

The immune system is an essential component of all animal beings. In mammals, in particular, it serves for defense against microorganisms, tissue regeneration and destruction of tumor cells. In classical immunology, distinction is made between cellular and humoral immune defense. This means two distinguishable, but cooperating systems which ultimately represent the immune system.

A number of diseases exist which, due to their pathogenesis, are considered auto-immune diseases. In such diseases, the immune system of the afflicted subjects is directed against their own organs, tissues, cells or proteins and other molecules. The predominantly cell-mediated auto-immune diseases include multiple sclerosis and diabetes (type I).

A second group are the predominantly antibody-mediated auto-immune diseases. These include, for example, rheumatism, the less frequently occurring auto-immune diseases, such as myasthenia gravis or lupus erythematodes, and recently also dilatative cardiomyopathy (DCM).

The pathogenesis of most auto-immune diseases is unknown. There are various hypotheses and models of how to explain the genesis of auto-immune diseases. One explaining model is antigenic/molecular mimicry. In this model, it is considered that microorganisms, e.g., viruses or parasites, provide themselves with particular molecules which are, for example, remarkably similar to or even in part identical with endogenous structures of the host and are therefore not recognized by the immune system of the host.

However, when they are recognized as foreign and antibodies are produced against them, then such antibodies will also recognize similar endogenous structures, which results in activation of the immune system and complement system. This induces pathological reactions in situ in the tissue, for example, chronic inflammations, or a pathological dysfunction of the cells occurs to which the auto-antibodies have bound.

Dilatative cardiomyopathy can be considered a prominent example thereof. In this auto-immune disease, the organisms erroneously forms antibodies which bind to defined regions of $\beta_1$-adrenergic receptor. These regions are on the first and second loops of a total of three extracellular loops of $\beta_1$-adrenergic receptor.

Such auto-antibodies which are capable to bind to these regions cause an increase of the pulsation rate in biological tests with rat cardiomyocytes in a cell culture (these cells have a nearly identical $\beta_1$-adrenergic receptor on their surface). This is referred to as a pharmaco-active effect of the auto-antibodies similar to that of adrenalin. The auto-antibodies directed against the epitopes on loops 1 and 2 of the $\beta_1$-adrenergic receptor are mainly observed in patients suffering from DCM. Occasionally, such auto-antibodies are also observed in patients having cardiac dysrhythmia and myocarditis.

Dilatative cardiomyopathy is an auto-immune disease which, when not treated, results in a severe deterioration of the cardiac output, i.e., reduction of the pumping output with simultaneous expansion of the myocardiac tissue by infiltrates, and then in heart transplantation or death.

However, if the antibodies are removed from the patient's blood by lavage of the blood, regeneration of the heart muscle and a dramatic improvement of the myocardiac output, which almost reaches the values of healthy people, occur within one year.

In patients with DCM, an immunoglobulin fraction which contains the specific auto-antibodies binding to $\beta_1$-adrenergic receptor and thereby activate the cell can be isolated from the plasma. When peptides of $\beta_1$-adrenergic receptor which represent the binding site for the auto-antibodies are added to a cell culture of rat cardiomyocytes, the pathological effect of the immunoglobulin fraction can be neutralized.

If the same peptides which correspond to the native sequences are coupled to a solid phase, they are no longer capable of binding and eliminating the auto-antibodies described from a patient's blood plasma. This means that the peptides which correspond to the native sequence of $\beta_1$-adrenergic receptor and represent binding sites for the pathological auto-antibodies described cannot be used for immuno-adsorption.

It has been the object of the invention to provide peptides which recognize, bind and eliminate pathological auto-antibodies directed against functional epitopes in the blood or plasma of patients having a positive antibody state or DCM, wherein the peptides, in addition to the epitopes which respectively neutralize the antibody effect, simultaneously contain amino acid sequences which enable binding of the pathological antibodies.

Surprisingly, this object is achieved by peptides having the amino acid sequence

X01-X02-X03-G-X04-X05-X06-X07-X08-X09-W-X10-X11-X12 wherein

X01=amino group, acetyl group, biotin group, fluorescent label, spacer, linker or deletion;
X02=D, G, E, T, S or deletion;
X03=W, Y, F, G, T;
X04=T, S, A, G;
X05=L, F, Y, W;
X06=V, I, W, F, Y;
X07=S, A, C;
X08=G, D, E, N, Q;
X09=F, L, I, Y;
X10=E, Q, T, S, L;
X11=Y, F, T, S, W;
X12=amide, the free acid, GKK, or a spacer;

and peptides having the amino acid sequence
X01-X02-W-X03-R-X04-X05-X06-X07-X08-E-A-R-X09-X10-X11-X12-X13-X14-X15-X16-X17 wherein
X01=amino group, amino acid, peptide, acetyl group, biotin group, fluorescent label, spacer, linker or deletion;
X02=H, E, Q;
X03=H, F, Y, W;
X04=A, V;
X05=G, T, E, S, D, N;
X06=S, H, A;
X07=D, N, Q, E;
X08=G, A, or a deletion;
X09=D, N, R;
X10=S, T, C, M;
X11=H F, W, Y;

X12=A, D, N, S;
X13=D, N;
X14=E, P;
X15=R, K, T;
X16=S, T, C, M or a deletion;
X17=amide, the free acid, GKK, SGKK or a spacer.

In particular, peptides according to the invention having the following amino acid sequence are employed:
X01-X02-X03-G-X04-X05-X06-X07-X08-X09-W-X10-X11-X12 wherein
X01=amino group, acetyl group, biotin group, fluorescent label, spacer, linker or deletion;
X02=D, E, T, or deletion;
X03=W, Y, T;
X04=T, S;
X05=L, F;
X06=V, F;
X07=S;
X08=G, D, E;
X09=F, L;
X10=E, Q, T, L;
X11=Y, T, S;
X12=amid, the free acid, GKK, or a spacer;

and peptides having the amino acid sequence
X01-H-W-X03-R-A-X05-S-D-X08-E-A-R-R-S-Y-X12-D-P-X15-X16-X17 wherein
X01=amino group, amino acid, peptide, acetyl group, biotin group, fluorescent label, spacer, linker or deletion;
X03=Y, W;
X05=T, E;
X08=G, or a deletion;
X12=A, N;
X15=K, T;
X16=S, or a deletion;
X17=amide, the free acid, GKK, SGKK or a spacer.

It is particularly preferred to employ the following peptides which are selected from the group consisting of
-TGSFFSELWTSR$^2$,
EYGSFFSELWTSR$^2$,
TYGTLFSDFWLSR$^2$,
DWGTLVSGFWEYR$^2$,
DWGTLFSDFWQTR$^2$, wherein R$^2$ is an acid amide, a free acid or GKKR$^3$, and wherein R$^3$ is an acid amide or a free acid;

with the proviso that a maximum of one non-conservative amino acid exchange is effected per amino acid position in the sequence, wherein "non-conservative exchange" means an exchange of amino acids between the groups mentioned below:
Group I: Leu, Ile, Val, Met, His, Trp, Tyr, Phe,
Group II: Glu, Gln, Asp, Asn,
Group III: Ser, Thr, Cys, Gly, Ala, Pro,
Group IV: Lys, Arg;

and peptides selected from the group consisting of:
HWWRAESD-EARRSYNDPK-R$^2$,
HWYRATSDGEARRSYADPTSR$^2$, with the proviso that a maximum of two non-conservative amino acid exchanges are effected per amino acid position in the sequence, wherein "non-conservative exchange" means an exchange of amino acids between the groups mentioned below:
Group I: Leu, Ile, Val, Met, His, Trp, Tyr, Phe,
Group II: Glu, Gln, Asp, Asn,
Group III: Ser, Thr, Cys, Gly, Ala, Pro,
Group IV: Lys, Arg.

The following peptides are particularly preferred:
TGSFF SELWT SGKK-amide or free acid, (SEQ. ID. NO. 1)
E YGSFF SELWT SGKK-amide or free acid, (SEQ. ID. NO. 2)
T YGTLF SDFWL SGKK-amide or free acid, (SEQ. ID. NO. 3)
His-Trp-Trp-Arg-Ala-Glu-Ser-Asp-Glu-Ala-Arg-Arg-Ser-Tyr-Asn-Asp-Pro-Lys-amide or free acid, (SEQ. ID. NO. 4)
Ala-Arg-Arg-Cys-Tyr-Asn-Asp-Pro-Lys-amide or free acid, (SEQ. ID. NO. 5)
D WGTLV SGFWE Y amide or free acid, (SEQ. ID. NO. 6)
D WGTLF SDFWQ TGKK amide or free acid, (SEQ. ID. NO. 7)
H WYRAT SDGEA RRSYA DPTSG KK-amide or free acid, (SEQ. ID. NO. 8)
HWWRAESDEARRSYNDPKC-amide or free acid, (SEQ. ID. NO. 9)

which may also be acetylated N-terminally.

The skilled person knows that amino acid positions in peptides or proteins can be exchanged in a conservative manner without affecting the function. In the present case, a "conservative" exchange means an exchange within the groups set forth below:
Group I: Leu, Ile, Val, Met, His, Trp, Tyr, Phe,
Group II: Glu, Gln, Asp, Asn,
Group III: Ser, Thr, Cys, Gly, Ala, Pro,
Group IV: Lys, Arg.

The peptides according to the invention are bound, in particular, by antibodies of patients suffering from dilatative cardiomyopathy.

As a linker according to the invention, all structures may be used which are available for that purpose unless adversely affecting the binding behavior of the peptides towards the antibodies. Usually, a linker is a chemical compound which provides at least one linking site (functional group) on a polymeric matrix which is otherwise free of functions.

The linking site serves for coupling a ligand or a spacer and matches the chemical properties of the ligand or spacer. Such a link is stable or cleavable depending on the type of linker molecule.

A ligand is usually a compound having some special property. According to the invention, the ligand is preferably a peptide which is capable of specifically binding an auto-antibody which has an adrenergic activity and is directed against the β-adrenergic receptor of the heart muscle.

According to the invention, the following linkers are preferably employed:
α-aminocarboxylic acids and their homo- and heterooligomers, α,ω-amino-carboxylic acids and their branched homo- or heterooligomers, other amino acids and their linear and branched homo- or heterooligomers (peptides); amino-oligoalkoxy-alkylamines; maleinimidocarboxylic acid derivatives; oligomers of alkylamines; 4-alkylphenyl derivatives; 4-oligoalkoxyphenyl or 4-oligoalkoxy-phenoxy derivatives; 4-oligoalkylmercaptophenyl or 4-oligoalkylmercaptophenoxy derivatives; 4-oligoalkylaminophenyl or 4-oligoalkylaminophenoxy derivatives; (oligoalkylbenzyl)phenyl or (4-oligoalkylbenzyl)phenoxy derivatives, and (4-oligoalkoxybenzyl)phenyl or (4-oligoalkoxybenzyl)phenoxy derivatives; trityl derivatives; benzyloxyaryl or benzyloxyalkyl derivatives; xanthene-3-yloxyalkyl derivatives; (4-alkylphenyl) or ω-(4-alkylphenoxy)alkanoic acid derivatives; oligoalkylphenoxyalkyl or oligoalkoxyphenoxyalkyl derivatives; carbamate derivatives; amines; trialkylsilyl or dialkylalkoxysilyl derivatives; alkyl or aryl derivatives, and combinations thereof.

In particular, the peptides according to the invention are bound to a solid phase for use. Preferably, the binding of the peptides to the solid phase is effected through a spacer. As the spacer, there may be used virtually all chemical compounds or groups suitable for such a function unless adversely affecting the binding behavior to such an extent that binding of the antibody with the peptide is prevented or substantially impaired.

A spacer is usually a compound which is inserted between a ligand and a linker if necessary and serves for positioning the ligand at a distance and in a spatial position appropriate for the binding of the auto-antibody. Spacers are molecules having at least two chemically active groups (functional groups), of which one group binds to the linker molecule, and at least one second functional group mediates binding to a ligand. By selecting the spacer, an increase of flexibility and an improvement of accessibility as well as an oriented arrangement of the ligands and increase of ligand density on the surface can be achieved depending on requirements.

Spacers include, for example, ω-aminocarboxylic acids and their homo- and heterooligomers, α,ω-aminocarboxylic acids and their branched homo- or heterooligomers, other aminocarboxylic acids and their linear and branched homo- or heterooligomers, maleinimidocarboxylic acid derivatives, hydroxycarboxylic acid derivatives, dicarboxylic acid derivatives, diamine derivatives dihydroxyalkyl derivatives, and hydroxyalkylamine derivatives. Preferably, mono- or dioligomers of β-alanine or ω-aminohexanoic acid and branched mono- or dioligomers of lysine or ornithine are used. The technology by means of which peptides can be anchored to solid phases is per se known to the skilled person.

In another embodiment of the invention, the peptides according to the invention are employed as medicaments.

In this concept, peptides are particularly altered (e.g. by cyclization) so that they cannot be destroyed by serum proteases and will bind antibodies in solutions. In this way, in-vivo neutralization of the antibodies can take place by intravenously administering the correspondingly processed peptides. The peptides are to be considered as medicaments herein. Their development is directly derived from the peptides binding the antibodies, which are fixed to a column matrix.

The amount of peptides to be administered depends on their molecular weight (i.e., their size) and on the concentration of auto-antibodies which can be reached in the blood stream and other compartments. According to what is known today, the amounts of auto-antibodies are within the μg and ng ranges. A quantity of between 1 and 5 μg of peptide should be sufficient for binding the antibodies present and pass them to elimination as an immune complex in accordance with the natural clearance mechanisms. Subsequently, the dosages can be lower since only the newly produced antibodies must be eliminated.

In principle, other dosage forms may be suitable in this case too. When the corresponding galenic methods are used, absorption in the intestine of peptides binding $\beta_1$-adrenergic antibodies should be achievable. In this case, the dosages would preferably be higher by a factor of about 10 to 20.

The peptides according to the invention can be employed for the preparation of a medicament for treatment of diseases related to $\beta_1$-adrenergically active auto-antibodies, especially dilatative cardiomyopathy, blood hypertension diseases, and a form of cardiomyopathy induced by *Trypanosoma cruzi*. In addition to dilatative cardiomyopathy, a number of diseases exist which can be classified as autoimmune diseases and are subject to similar pathomechanisms. Also for pre-eclampsia and certain forms of malignant blood hypertension, auto-antibodies have been described which contribute to the hyperactivation of cells by stimulating their angiotensin receptor or $\alpha_1$ receptor, and participate in the genesis of defined clinical pictures. The use of peptides for eliminating these specific auto-antibodies or for in-vivo neutralization of the auto-antibodies can be regarded by analogy with dilatative cardiomyopathy.

According to the invention, a method is claimed for the treatment of diseases related to $\beta_1$-adrenergically active auto-antibodies by removing the auto-antibodies using peptides bound to a solid phase. Advantageously, this may be effected with a device for chromatography according to the invention containing the peptides according to the invention bound to a solid phase.

The peptides are fixed to a solid phase, e.g., sepharose, in a closed sterile container which usually has a volume of between 5 and 250 ml. In this sterile space, the patients' blood plasma, from which the cells have previously been removed by a medical engineering apparatus, flows over or through the adsorption matrix, i.e., the peptide-coated sepharose surface. This results in the binding of the pathological auto-antibodies to the peptides which simulate regions of the $\beta_1$-adrenergic receptor. If suitable adsorption matrices are employed, the previous separation of the cells can be dispensed with.

The remaining components of the blood plasma or blood including all necessary and useful immunoglobulins then leave the column and are recirculated into the patient's blood stream. This device for extracorporeal therapy is state of the art as far as the non-specific elimination of plasma proteins or immunoglobulin is concerned.

The device according to the invention uses the peptides derived from the $\beta_1$-adrenergic receptor for removing the small but pathologically relevant auto-antibody fraction from the plasma.

After a certain amount of blood plasma has flown through the device, the blood plasma stream can be switched over to a second column which is technically identical with the first, while the first column is being regenerated. That means, the loaded antibodies are separated from the peptide and discarded by using different rinsing and elution solutions, preferably physiological saline with and without additional buffering, for example, by phosphate, glycine or citrate, and a pH range of from pH 2 to pH 7.5. Subsequently, the thus regenerated column is again available for the binding and elimination of the pathological auto-antibodies from the patient's blood plasma. This double column principle has proven useful and is always used when regeneration of the column is required.

A second variant of the use of peptides for the elimination of pathological auto-antibodies includes the use of disposable columns. In these columns, the solid-phase matrix contains an amount of peptide sufficient that major portions of the auto-antibodies can be removed from the plasma in several hours of treatment. The advantage resides in the fact that the time-consuming and tedious regeneration of the adsorption matrix can be dispensed with.

A third variant of the treatment of DCM patients by the elimination of pathological antibodies from the blood plasma includes the use of columns in which a previous separation of plasma and blood cells is not required due to the design of the columns.

The use of columns requires technical devices which ensure a blood and plasma input and flow adequate for the treatment by using different flexible tubes, pumps, monitor screens and other monitoring systems.

EXAMPLE

1. Peptides

The following two peptides were immobilized on cross-linked agarose beads Sepharose 4B as the solid phase.
Peptide 1: TGSFFCELWTSGKK
Peptide 2: HWWRAESDEARRSYNDPKC Sepharose CL4B served as the filling matrix. From the two peptide matrices and the filling matrix, an affinity chromatographic column was prepared, and its function, i.e., the removal of DCM-related auto-antibodies from human plasma, was tested with human plasma as a sample.

2. Immobilization of the Peptides

For immobilization on a solid phase, the peptides were dissolved in coupling buffer (0.5 M NaCl, 0.1 M NaHCO3, pH 8.3) to a concentration of 2 mg/ml, and mixed with washed and CNBr-preactivated Sepharose 4B. After completion of the coupling reaction, the peptide matrices were washed with coupling buffer, and the excess CNBr groups were inactivated.

The peptide loading of the matrices was determined photometrically by calculating the difference between the mass of peptide employed before the coupling and the mass of non-immobilized peptide after the coupling.

The matrix loading with peptide 1 was 2.0 mg of peptide/ml of matrix. The matrix loading with peptide 2 was 1.8 mg of peptide/ml of matrix.

To prepare the affinity chromatographic column, peptide matrix 1 and peptide matrix 2 were mixed at a ratio of 1:1, and this mixture was mixed with filling matrix at a ratio of 1:5. The total volume of the matrix for the affinity chromatographic column was 100 ml.

3. Removal of DCM-Related Auto-Antibodies from Human Plasma

The function of the above described affinity chromatographic column was tested on two persons afflicted with DCM and exhibiting a positive test for DCM-related auto-antibodies.

Prior to the application, the persons must be treated with anti-coagulants, such as heparin, hirudin or citrate.

Thus, from the recommended concentration range of from 1500 to 3000 units, a bolus of heparin of 2000 units was chosen for intravenous administration. During the application, from the recommended concentration range of from 250 to 750 units of heparin per hour, a dosage of 500 units of heparin per hour was chosen for intravenous administration.

The blood was passed into a separator in which the separation of the cellular components of the blood from the blood plasma was effected. The plasma of the persons testing positive for DCM-related auto-antibodies was passed over the affinity chromatographic column. The volume ratio of the affinity matrix to the plasma was between 1:6 and 1:10 for the affinity chromatographic column runs performed. All in all, 20 such purification cycles were performed, wherein the treated plasma was reinfused to the persons after each cycle together with the cellular blood components. The total number of purification cycles of 20 is derived from 4 purification cycles per day of application for a total of 5 days of application.

4. Quantitative Assay of the DCM-Related Auto-Antibodies

A quantitative assay of the DCM-related auto-antibodies was effected from plasma samples of the persons afflicted with DCM, obtained before and after the application on each day of application. The assay of the DCM-related auto-antibodies (antibodies against $\beta_1$-adrenergic receptor) was performed according to Wallukat, G., Wollenberger, A., Morwinski, R. and Pitschner, H. F. (1995); Anti-$\beta_1$-adrenoceptor antibodies with chronotropic activity from the serum of patients with dilated cardiomyopathy: mapping of epitopes in the first and second extracellular loops; J. Mol. Cell. Cardiol. 27, 397–406.

5. Results of the Removal of DCM-Related Auto-Antibodies from Human Plasma

For person 1 having auto-antibodies which preferably bind to peptide 1, a reduction of auto-antibodies to 12% of the initial value was achieved after completion of the overall application.

For person 2 having auto-antibodies which preferably bind to peptide 2, a reduction of auto-antibodies to 5% of the initial value was achieved after completion of the overall application.

The results for the overall application are set forth in Table 1.

In both persons, the concentrations of other plasma parameters, such as total protein, albumin and IgG, were almost unaffected during the overall application.

Table 1: DCM-related auto-antibodies (antibodies against $\beta_1$-adrenergic receptor) in the human plasma of person 1 and person 2 before, during and after treatment with the affinity chromatographic column.

After elution from the affinity matrix, the auto-antibodies bound to the affinity chromatographic column were tested for preferential binding to peptide 1 or peptide 2 by means of peptide 1 and peptide 2 bound to a solid phase. Auto-antibody type 1 prefers the binding of peptide 1, and auto-antibody type 2 prefers the binding of peptide 2.

| | Person 1 | |
|---|---|---|
| Plasma sample | Auto-antibody 2 [relative units] | Auto-antibody 2 [%] |
| before cycle 1–4 | 5.8 | 100 |
| after cycle 1–4 | 2.4 | 41 |
| before cycle 5–8 | 3.4 | 59 |
| after cycle 5–8 | 1.6 | 28 |
| before cycle 9–12 | 3.3 | 57 |
| after cycle 9–12 | 2.0 | 34 |
| before cycle 13–16 | 1.9 | 33 |
| after cycle 13–16 | 0.8 | 14 |
| before cycle 17–20 | 1.7 | 29 |
| after cycle 17–20 | 0.7 | 12 |

| Plasma sample | Person 2 Auto-antibody 2 [relative units] | Auto-antibody 2 [%] |
|---|---|---|
| before cycle 1–4 | 6.1 | 100 |
| after cycle 1–4 | 3.1 | 51 |
| before cycle 5–8 | 3.8 | 62 |
| after cycle 5–8 | 3.0 | 49 |
| before cycle 9–12 | 3.5 | 57 |

-continued

| Plasma sample | Person 2 Auto-antibody 2 [relative units] | Auto-antibody 2 [%] |
|---|---|---|
| after cycle 9–12 | 2.3 | 38 |
| before cycle 13–16 | 2.8 | 46 |
| after cycle 13–16 | 0.9 | 15 |
| before cycle 17–20 | 1.7 | 28 |
| after cycle 17–20 | 0.3 | 5 |

What is claimed is:

1. A compound consisting of
X01-Thr Gly Ser Phe Phe Ser Glu Leu Trp Thr Ser (SEQ ID NO: 1)-X12 or
X01-Glu Tyr Gly Ser Phe Phe Ser Glu Leu Trp Thr Ser (SEQ ID NO: 2)-X12,
wherein
X01=acetyl group, biotin group, fluorescent label, spacer, linker, or deletion;
X12=amide, the free acid, GKKR³, or a spacer,
wherein R³ is an acid amide or a free acid or a spacer.

2. The compound according to claim 1, characterized by being:
TGSFF SELWT SGKK-amide or free acid,
E YGSFF SELWT SGKK-amide or free acid, which may also be acetylated N-terminally.

3. The compound according to claim 1, characterized by being bound by antibodies of patients suffering from dilatative cardiomyopathy.

4. The compound according to claim 1, characterized in that said linker is selected from the group consisting of:
α-aminocarboxylic acids or their homo- and heterooligomers;
α,ω-aminocarboxylic acids or their branched homo- or heterooligomers;
other amino acids or their linear or branched homo- or heterooligomers (peptides);
amino-oligoalkoxy-alkylamines;
maleiriimidocarboxyllc acid derivatives;
oligomers of alkylamines;
4-alkylphenyl derivatives;
4-oligoalkoxyphenyl or 4-oligoalkoxyphenoxy derivatives;
4-oligoalkylmercaptophenyl or 4-oligoalkylmercaptophenoxy derivatives;
4-oligoalkylaminopheriyl or 4-oligoalkylaminophenoxy derivatives;
(4-oligoalkylbenzyl)phenyl or (4-oligoalkylbenzyl)phenoxy derivatives;
(4-oligoalkoxybenzyl)phenyl or (4-oligoalkoxybenzyl) phenoxy derivatives;
trityl derivatives;
benzyloxyaryl or benzyloxyalkyl derivatives;
xanthene-3-yloxyalkyl derivatives;
(4-alkylphenyl) or o-(4-alkylphenoxy)alkanoic acid derivatives;
oligoalkylphenoxyalkyl or oligoalkoxyphenoxyalkyl derivatives;
carbamate derivatives;
amines;
trialkylsilyl or dialkylaIkoxysilyl derivatives;
alkyl or aryl derivatives; and
combinations thereof.

5. The compound according to claim 1, characterized by being bound to a solid phase.

6. The compound according to claim 1, characterized by being bound to a solid phase through a spacer.

7. A medicament for treatment of dilatative cardiomyopathy containing the compound according to claim 1 in combination with a carrier.

8. A method of treating dilatative cardiomyopathy comprising administering to a patient the medicament according to claim 7.

9. A method of dilatative cardiomyopathy therapy comprising removing $\beta_1$, adrenergically active auto-antibodies from a patient's blood by extracorporeal treatment with the compound according to claim 4 bound to a solid phase.

10. A device for chromatography comprising the compound according to claim 4 bound to a solid phase.

* * * * *

SEQUENCE LISTING

<160> NUMBER OF SEQ ID NOS: 16

<210> SEQ ID NO 1
<211> LENGTH: 11
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 1

Thr Gly Ser Phe Phe Ser Glu Leu Trp Thr Ser
1               5                   10

<210> SEQ ID NO 2
<211> LENGTH: 12
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 2

Glu Tyr Gly Ser Phe Phe Ser Glu Leu Trp Thr Ser
1               5                   10

<210> SEQ ID NO 3
<211> LENGTH: 12
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 3

Thr Tyr Gly Thr Leu Phe Ser Asp Phe Trp Leu Ser
1               5                   10

<210> SEQ ID NO 4
<211> LENGTH: 12
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 4

Asp Trp Gly Thr Leu Val Ser Gly Phe Trp Glu Tyr
1               5                   10

```
<210> SEQ ID NO 5
<211> LENGTH: 12
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 5

Asp Trp Gly Thr Leu Phe Ser Asp Phe Trp Gln Thr
1               5                   10

<210> SEQ ID NO 6
<211> LENGTH: 18
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 6

His Trp Trp Arg Ala Glu Ser Asp Glu Ala Arg Arg Ser Tyr Asn Asp
1               5                   10                  15

Pro Lys

<210> SEQ ID NO 7
<211> LENGTH: 20
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 7

His Trp Tyr Arg Ala Thr Ser Asp Gly Glu Ala Arg Arg Ser Tyr Ala
1               5                   10                  15

Asp Pro Thr Ser
            20

<210> SEQ ID NO 8
<211> LENGTH: 14
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 8

Thr Gly Ser Phe Phe Ser Glu Leu Trp Thr Ser Gly Lys Lys
1               5                   10

<210> SEQ ID NO 9
<211> LENGTH: 15
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 9

Glu Tyr Gly Ser Phe Phe Ser Glu Leu Trp Thr Ser Gly Lys Lys
1               5                   10                  15

<210> SEQ ID NO 10
<211> LENGTH: 15
<212> TYPE: PRT
```

```
<213> ORGANISM: Artificial sequence
<220> FEATURE:
<223> OTHER INFORMATION: Peptides against DCM-causing autoimmuno-
      antibodies

<400> SEQUENCE: 10

Thr Tyr Gly Thr Leu Phe Ser Asp Phe Trp Leu Ser Gly Lys Lys
1               5                   10                  15

<210> SEQ ID NO 11
<211> LENGTH: 18
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 11

His Trp Trp Arg Ala Glu Ser Asp Glu Ala Arg Arg Ser Tyr Asn Asp
1               5                   10                  15

Pro Lys

<210> SEQ ID NO 12
<211> LENGTH: 9
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 12

Ala Arg Arg Cys Tyr Asn Asp Pro Lys
1               5

<210> SEQ ID NO 13
<211> LENGTH: 12
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 13

Asp Trp Gly Thr Leu Val Ser Gly Phe Trp Glu Tyr
1               5                   10

<210> SEQ ID NO 14
<211> LENGTH: 15
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 14

Asp Trp Gly Thr Leu Phe Ser Asp Phe Trp Gln Thr Gly Lys Lys
1               5                   10                  15

<210> SEQ ID NO 15
<211> LENGTH: 23
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 15
```

```
                          -continued

His Trp Tyr Arg Ala Thr Ser Asp Gly Glu Ala Arg Arg Ser Tyr Ala
1               5                   10                  15

Asp Pro Thr Ser Gly Lys Lys
            20

<210> SEQ ID NO 16
<211> LENGTH: 19
<212> TYPE: PRT
<213> ORGANISM: Artificial sequence
<220> FEATURE:
<223> OTHER INFORMATION: Peptides against DCM-causing autoimmuno-
      antibodies

<400> SEQUENCE: 16

His Trp Trp Arg Ala Glu Ser Asp Glu Ala Arg Arg Ser Tyr Asn Asp
1               5                   10                  15

Pro Lys Cys
```